United States Patent [19]

Hamacher

[11] Patent Number: 4,790,830
[45] Date of Patent: Dec. 13, 1988

[54] INFUSION NEEDLE

[76] Inventor: Edward N. Hamacher, 725 South Lincoln, Apt. C-4, Spokane, Wash. 99204

[21] Appl. No.: 77,493

[22] Filed: Jul. 24, 1987

Related U.S. Application Data

[63] Continuation of Ser. No. 718,159, Apr. 1, 1985, Pat. No. 4,699,612.

[51] Int. Cl.⁴ .............................................. A61M 5/32
[52] U.S. Cl. ...................... 604/274; 604/239; 604/264; 128/339; 128/348.1
[58] Field of Search ............... 604/49, 51–54, 604/93, 187, 164–170, 239, 264, 272, 274, 280, 283, 902; 128/329 R, 339, 340, 348.1

[56] References Cited

U.S. PATENT DOCUMENTS

| | | | |
|---|---|---|---|
| 806,746 | 12/1905 | Miller | 604/274 |
| 2,634,726 | 4/1953 | Hanson | 604/274 |
| 2,862,495 | 12/1958 | Gewecke | 604/274 |
| 3,181,336 | 5/1965 | Schofield | 72/340 |
| 3,369,542 | 2/1968 | Thaidigsman | 604/280 |
| 3,840,008 | 10/1974 | Noiles | 604/51 |
| 3,854,477 | 12/1974 | Smith | 604/51 |
| 4,246,894 | 1/1981 | Hamacher | 128/1 R |
| 4,334,526 | 6/1982 | Hamacher | 128/1 R |
| 4,405,308 | 9/1983 | Jessup | 604/200 |
| 4,411,657 | 10/1983 | Galindo | 604/274 |
| 4,413,993 | 11/1983 | Guttman | 604/274 |
| 4,453,928 | 6/1984 | Steiger | 604/264 |

OTHER PUBLICATIONS

RANFAC Hypodermic Instruments Booklet.

Primary Examiner—C. Fred Rosenbaum
Assistant Examiner—Mario Costantino
Attorney, Agent, or Firm—Seed and Berry

[57] ABSTRACT

A method and an appartus for safely infiltrating an area of subcutaneous tissue from a single entry point with an elongated needle which avoids puncturing blood vessels. The needle is substantially blunt so as to be capable of penetrating subcutaneous tissue and to divert blood vessels around the needle on insertion. Toxic local anesthetics can be injected during insertion of the needle without having to first retract the needle to verify that a blood vessel has not been punctured.

12 Claims, 1 Drawing Sheet

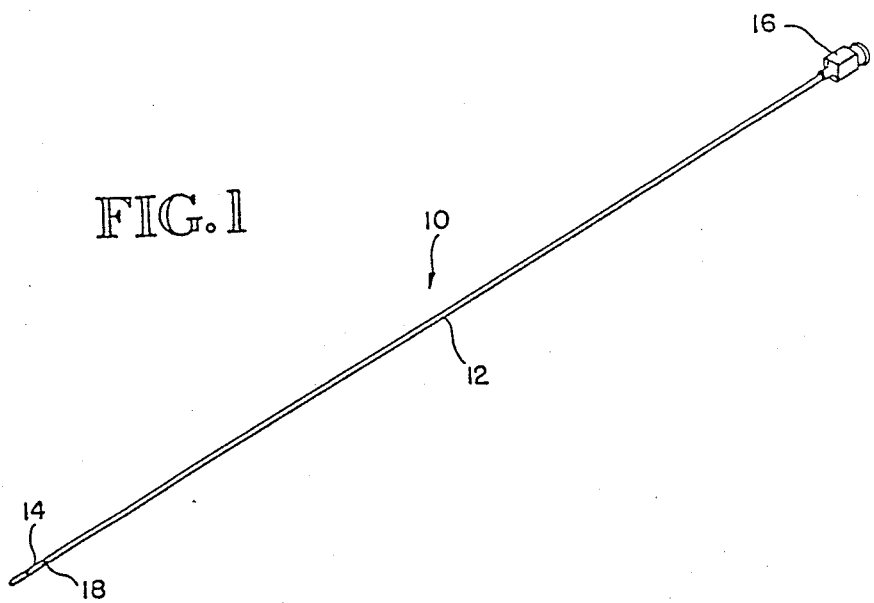
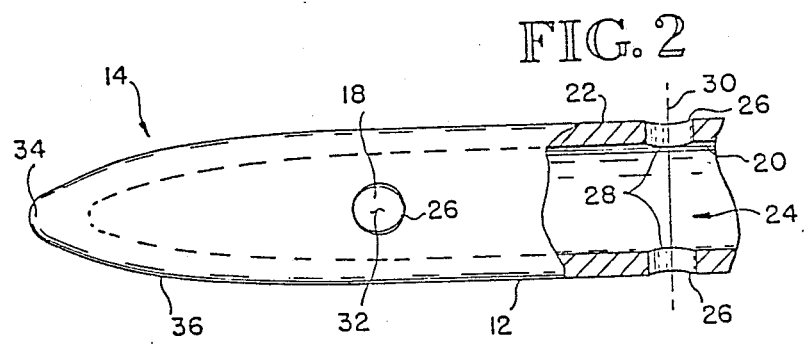
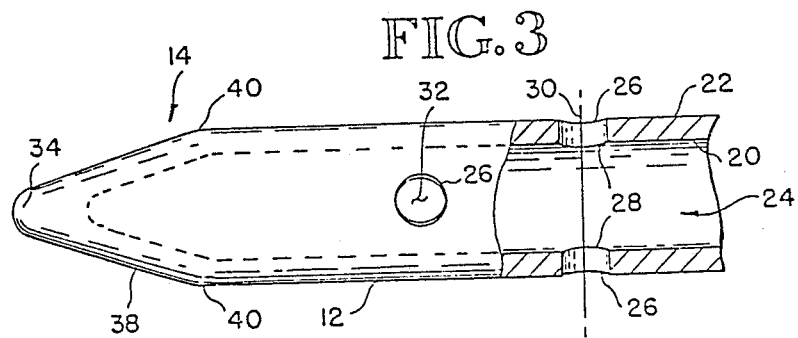

INFUSION NEEDLE

This application is a continuation of U.S. patent application Ser. No. 718,159, filed Apr. 1, 1985, now U.S. Pat. No. 4,699,612.

TECHNICAL FIELD

The invention relates to an apparatus and a method for area infiltration of subcutaneous tissue. Specifically, the invention relates to a method and an apparatus for infiltrating an area of subcutaneous tissue from a single entry point with a needle which can (1) easily traverse through the subcutaneous tissue, (2) avoid puncturing blood vessels, and (3) create a good dissecting plane.

BACKGROUND ART

Area infiltration of subcutaneous tissue with anesthetics or other fluids is well known, especially in the field of reconstructive surgery. Patients often remain conscious during this type of surgery, requiring the specific localized area to be anesthesized. Various needles of conventional design are presently available to infiltrate these areas with local anesthesia or other fluids. Some of the anesthetics and other fluids used in these procedures, such as lidocaine HCl, commonly available under the brand name Xylocane, or benzocaine, are highly toxic to the patient and can create serious problems if the medicine is injected into the bloodstream instead of the subcutaneous or fatty tissue. Therefore, with conventional needles, great care must be taken to assure that a blood vessel is not punctured and injected with a toxic substance.

A standard procedure has been developed by physicians to prevent the injection of toxic fluids into blood vessels during area infiltration of subcutaneous tissue. The needle is inserted into the tissue to the desired position. The needle is then retracted slightly and the syringe piston is displaced so as to create a partial vacuum within the syringe. If a blood vessel has been punctured, the syringe will fill with blood, providing a visual verification that a vessel has been punctured. If, upon retraction of the needle, the syringe does not fill with the blood, then it is apparent that a vessel has not been punctured and injection of the fluid may proceed. Slight retraction of the needle after insertion is required to assure that a vessel has not been punctured; otherwise, the aperture of the needle may be in contact with an interior vessel wall. The contact between the needle aperture and the inner wall can seal the needle aperture preventing blood from flowing through the needle into the syringe. This procedure is time-consuming for the physician and can result in increased pain for the patient since injection of an anesthetic, is precluded until the needle has been fully inserted and slightly retracted to check for the presence of blood in the syringe.

In addition to the extra time required and pain which a patient must undergo while an area is anesthetized in the conventional manner, the patient is also subjected to multiple skin punctures caused by the needle since the needle is normally inserted in a variety of places in order to infuse a relatively large area. Patients undergoing this type of treatment usually suffer from hematomas due to the large number of punctures made.

DISCLOSURE OF INVENTION

It is an object of the invention to significantly reduce injection hematomas during area infiltration of subcutaneous tissue.

It is also an object of the invention to reduce the pain experienced by a conscious patient during the anesthetization of subcutaneous tissue when using a toxic local anesthetic.

It is a further object of the invention to allow a physician to inject the toxic medicines into subcutaneous tissue while inserting the needle without having to first retract the needle to verify that a blood vessel has not been punctured.

The invention achieves these objectives by providing an elongated needle having a blunt, bullet-like, tip which is capable of penetrating subcutaneous tissues without penetrating blood vessels. Thus a physician may inject toxic local anesthetics, such as lidocaine HCl, into subcutaneous tissues for area infiltration while the needle is being inserted, thus significantly reducing the pain experienced by the patient. Skin punctures are eliminated. Dermis entry is made by a small knife incision. Only several such entry sites are required and they are later closed with a suture, thereby, preventing multiple subcutaneous injection hematomas. Furthermore, a large area may be infiltrated from a single penetration of the dermis since the needle can be very long and can be routed within the subcutaneous tissue in a variety of directions without the danger of penetrating a blood vessel.

The needle has an elongated, substantially rigid shaft of constant radius having an inner surface and an outer surface. The inner surface defines a longitudinal fluid conduit for trnasporting fluids to the subcutaneous tissue. A tip, located at one end of the shaft, has a substantially blunt end for diverting blood vessels around the shaft on insertion to avoid puncturing the blood vessels. However, the blunt end is capable of penetrating the subcutaneous or fatty tissue. A conventional incision or other puncture must be made in the dermis to permit insertion of the needle into the subcutaneous tissue. The needle can then be routed to various areas within the subcutaneous tissue from this single incision. A local anesthetic or other fluid can be injected into the subcutaneous tissue while the needle is being inserted. Since the needle is almost incapable of penetrating blood vessel and is designed to divert blood vessels around the shaft, toxic fluids or anesthetics, such as lidocaine HCl, can be immediately injected without first having to fully insert slightly retract the needle, and check for the presence of blood in the syringe to verify that a vessel has not been punctured. Thus patients are not subject to the pain associated with fully inserting a needle into the subcutaneous tissue and slightly retracting the needle to check for the presence of blood within the syringe before the anesthetic can be injected. By reducing the possibility of trauma or puncturing to the blood vessel during insertion, the needles can be made unusually long, allowing the needle to reach a variety of locations from a single incision. Thus the patient is also relieved from the pain associated with using a shorter needle which is inserted at various points in the area with the attendant punctures at these insertion points.

The blunt end of the tip can form a vertex having a shape which is a portion of a spherical surface and wherein the vertex intersects the longitudinal axis of the shaft. In one embodiment, the tip has a substantially curved, smooth surface between the vertex and the shaft.

In another embodiment, the tip has a substantially smooth, straight surface forming a frustum between the vertex and the shaft. The intersection of the straight surface with the shaft is substantially curved and smooth to avoid damaging blood vessels when the needle is inserted.

In either embodiment, a plurality of openings can be provided near the tip of the needle to allow fluids to exit the fluid conduit in all direction including both laterals, the superior and inferior within the shaft.

BRIEF DESCRIPTION OF THE DRAWINGS

FIG. 1 is an isometric view of an infusion needle in accordance with the present invention.

FIG. 2 is an enlarged, partial, sectional elevation of the tip portion of the needle of FIG. 1, wherein the tip portion has substantially curved, smooth sides.

FIG. 3 is an enlarged, partial, sectional elevation of the needle of FIG. 1, wherein the tip portion has substantially straight sides.

BEST MODE FOR CARRYING OUT THE INVENTION

Referring now in detail to the drawing, the numerals herein refer to like-numbered parts in the figures.

In FIG. 1, an infusion needle, in accordance with the present invention, is generally indicated at reference numeral 10. The needle has an elongated shaft 12 of substantially constant diameter, a tip portion 14, and a connector portion or hub 16. The length of the shaft can vary according to the desired application for the needle. Typically, for reconstructive surgery, the needle has a length between 6 and 14 inches but can range between 3 and 18 inches. The connector portion is adapted to connect the needle to a standard hypodermic syringe. The tip portion is substantially blunt so as to prevent the penetrating of blood vessels by diverting blood vessels around the shaft when the needle is inserted into subcutaneous tissue. The needle has at least one outlet 18 to allow fluids to exit the needle.

As shown in FIG. 2, the shaft 12 has an inner surface 20 and an outer surface 22. The outer surface is substantially smooth throughout the length of the needle to prevent damage to tissue. The inner surface defines a longitudinal fluid conduit 24 for transporting medicines or fluids through the needle. The outer surface has one or more apertures 26 which communicate with corresponding apertures 28 to form at least one outlet 18 for dispensing fluids in a substantially radial direction through the shaft. A pair of outlets may be radially opposed on the shaft so that an axis 30 passing through the center of each outlet is perpendicular to the longitudinal axis of the shaft. Furthermore, a plurality of radially opposed openings can be provided so that the additional pairs of openings have axes 32 which are radially positioned approximately 90 degrees from one another. It is preferred to position the outlets near the tip portion.

The needle 10, constructed in this manner, allows a physician to insert the needle into the subcutaneous tissue and simultaneously inject the tissue with a toxic medicine, such as lidocaine HCl, without having to first verify that a blood vessel has not been punctured. Furthermore, since the dermis must be incised or otherwised punctured to provide an entry point for the needle, the physician is encouraged to reroute the needle through the subcutaneous tissue from the initial entry point because the tip portion is blunt and incapable of puncturing blood vessels and diverts blood vessels around the shaft as the needle is inserted further into the subcutaneous tissue. Thus, a large subcutaneous area can be infiltrated with anesthetic from a single incision and the anesthetic can be immediately applied to the area while the needle is being inserted, as well as during withdrawal, reducing the discomfort usually associated with this process. Additionally, the patient is only subjected to the trauma associated with the single incision or puncture in the dermis.

To prevent penetration of blood vessels on insertion and to encourage diverrion of blood vessels around the tip portion, the needle can be constructed from a variety of materials, including 14-gauge stainless steel, so that the needle is substantially rigid. The needle is also reusable and can be autoclaved to provide a sterile instrument.

As shown in FIGS. 2 and 3, the tip has a vertex 34 which intersects the longitudinal axis of the shaft. It is preferred that the vertex form a portion of the spherical surface having a radius of curvature sufficiently large to prevent the penetration of blood vessels when the needle is inserted into subcutaneous tissue. It is highly preferred that the radius of curvature be in the range of 0.178 mm to 0.245 mm. The vertex and tip portion are unitary and are formed, for example, by adding additional material to one end of a piece of 14-guage stainless steel tubing by heliarc shut welding the tip portion.

In one embodiment, shown in FIG. 2, the tip portion 14 has a substantially curved, smooth surface 36 between the vertex 34 and the shaft 12 to divert blood vessels around the shaft on insertion.

In a second embodiment, shown in FIG. 3, the tip portion 14 has a substantially smooth, straight surface 38 between the vertex 34 and the shaft 12 forming a frustoconic section between the vertex and the shaft. In this embodiment, the intersection of the straight surface with the shaft forms a curved shoulder 40 to avoid damaging blood vessels when the needle is inserted.

The various embodiments of the needle 10 allow a physician to safely inject toxic medicines for area infiltration during insertion, retraction, or both, without risk of penetrating blood vessels.

It will be appreciated that other variations and embodiments of the invention are contemplated. These additional embodiments have the same characteristics as the embodiments herein described. Therefore, the scope of the invention is not to be limited to the above description but is to be determined by the claims which follow.

I claim:

1. An infusion needle for use in area infiltration applications, and for preparation of a dissection plane, which reduces trauma to blood vessels during the injection process, comprising:
    (a) a longitudinally extending, substantially rigid, cylindrical shaft of substantially constant diameter having a length between 3 and 18 inches to allow injection of fluid in a plurality of directions for infiltrating a large subcutaneous area from a single entry point through the dermis, and having an inner surface and an outer surface, the inner surface defining a longitudinal fluid conduit for transporting fluids to subcutaneous tissue;
    (b) means, forming a tip portion, at one end of the shaft for penetrating and guiding the shaft through and along a substantial length of subcutaneous tissue and for diverting blood vessels around the shaft on insertion and penetration to avoid puncturing and damaging said vessels, wherein the tip portion forms a substantially blunt tip having a vertex which intersects and which is symmetrical about the longitudinal axis of the shaft and forms a portion of a curved surface so that the dermis must be incised to provide an entry point for the needle to encourage area infiltration of subcutaneous tissue from a single entry point, wherein the ratio of the vertex of curvature to the shaft diameter is in the range of approximately 0.1093:1 to 0.1504:1; and (c) a portion of the outer surface communicating with a corresponding portion of the inner surface defining at least one outlet for dispensing fluids in a substantially radial direction from the shaft.

2. A needle, as claimed in claim 1, wherein the fluid-dispensing outlet is on the shaft near the tip portion.

3. A needle, as claimed in claim 2, wherein the inner and outer surfaces of the shaft include second portions defining an additional outlet to form a pair of radially opposed outlets and wherein an axis passing through the centers of the outlets is perpendicular to the longitudinal axis of the shaft.

4. A needle, as claimed in claim 3, wherein the inner and outer surfaces of the shaft have additional portions defining two pairs of radially opposed outlets, each pair of outlets radially disposed approximately 90 degrees from one another.

5. A needle, as claimed in claim 1, wherein the shaft has an American Wire Gage size of 14 and a corresponding diameter of approximately 1.628 mm and the tip portion has a vertex which forms a portion of a curved surface having a radius of curvature in the range of 0.178 mm to 0.245 mm to prevent pentration of blood vessels on insertion, guide the shaft through the subcutaneous tissue and encourage diversion of blood vessels around the tip portion.

6. A needle, as claimed in claim 1, wherein the tip portion has a curved, smooth surface forming a transition zone between the vertex and the shaft.

7. A needle, as claimed in claim 6, wherein the shaft has an American Wire Gage size of 14 and a corresponding diameter of approximately 1.628 mm and the vertex curved surface has a radius of curvature in the range of 0.178 mm to 0.245 mm.

8. A needle, as claimed in claim 1, wherein the tip portion has a substantially smooth, straight surface forming a frustoconic transition zone between the vertex and the shaft, and wherein the intersection of the straight surface with the shaft is curved and smooth to avoid damaging blood vessels on insertion.

9. A needle, as claimed in claim 8, wherein the shaft has an American Wire Gage size of 14 and a corresponding diameter of approximately 1.628 mm and the vertex forms a portion of a curved surface having a radius of curvature in the range of 0.178 mm to 0.245 mm.

10. An infusion needle for use in area infiltration applications which reduces trauma to blood vessels during the injection process, comprising:

(a) a longitudinally extending, substantially rigid, cylindrical shaft having a substantially constant diameter between approximately 1.0 mm to 2.0 mm and having an inner surface and an outer surface, the inner surface defining a longitudinal fluid conduit for transporting fluids to subcutaneous tissue;

(b) a substantially blunt tip portion on one end of the shaft having means for penetrating and guiding the shaft along and through a substantial distance of subcutaneous tissue and for diverting blood vessels around the shaft on insertion to avoid puncturing and damaging said vessels so that the dermis must be incised to provide an entry point for the needle to encourage area infiltration of subcutaneous tissue from a single entry point;

(c) a vertex on the tip portion which intersects the longitudinal axis of the shaft and which forms a portion of a curved surface wherein the ratio of the vertex radius of curvature to the shaft diameter is in the range of approximately 0.1093:1 to 0.1504:1 to prevent penetration of blood vessels on insertion;

(d) a substantially smooth surface between the vertex and the shaft; and (e) a portion of the outer surface communicating with a corresponding position of the inner surface defining at least one outlet for dispensing fluid in a substantially radial direction from the shaft.

11. A needle, as claimed in claim 10, wherein the substantially smooth surface is a straight surface forming a frustoconic section between the vertex and the shaft, and wherein the intersection of the straight surface with the shaft is substantially curved and smooth to avoid damaging blood vessels on insertion.

12. A needle, as claimed in claim 10, wherein the substantially smooth surface is a curved surface between the vertex and the shaft.

* * * * *